(12) United States Patent
Gonsalves (10) Patent No.: US 11,766,573 B1
(45) Date of Patent: Sep. 26, 2023

(54) DEFIBRILLATOR WITH WARNING INDICATORS

(71) Applicant: Joseph Kjell Gonsalves, Falls Church, VA (US)

(72) Inventor: Joseph Kjell Gonsalves, Falls Church, VA (US)

( * ) Notice: Subject to any disclaimer, the term of this patent is extended or adjusted under 35 U.S.C. 154(b) by 50 days.

(21) Appl. No.: 17/073,369

(22) Filed: Oct. 18, 2020

(51) Int. Cl.
*A61B 5/02* (2006.01)
*A61N 1/39* (2006.01)
*G08B 21/18* (2006.01)
*G08B 3/10* (2006.01)

(52) U.S. Cl.
CPC .......... *A61N 1/3987* (2013.01); *A61N 1/3956* (2013.01); *G08B 3/10* (2013.01); *G08B 21/182* (2013.01)

(58) Field of Classification Search
CPC ...... A61N 1/3987; A61N 1/3956; G08B 3/10; G08B 21/182
See application file for complete search history.

(56) References Cited

U.S. PATENT DOCUMENTS

| | | | |
|---|---|---|---|
| 5,584,864 A * | 12/1996 | White | A61N 1/3956 607/5 |
| 2006/0259082 A1* | 11/2006 | Youker | A61N 1/3956 607/7 |
| 2011/0105860 A1* | 5/2011 | Houben | A61B 5/0205 607/18 |
| 2012/0081230 A1* | 4/2012 | Sullivan | G08B 21/24 340/636.1 |
| 2018/0035898 A1* | 2/2018 | Gunderson | A61N 1/39 |
| 2018/0185662 A1* | 7/2018 | Foshee, Jr | A61N 1/3993 |
| 2019/0069851 A1* | 3/2019 | Sharma | A61B 5/0031 |

* cited by examiner

*Primary Examiner* — Hongmin Fan (57) ABSTRACT

The patent application relates to an improved defibrillator device. The present invention compares the heart rate to a predetermined heart, rate from a medical professional so that it can warn the patient upon detecting early signs of heart failure, upon detecting significant signs of heart failure, and prior to shock administration. Such warnings would prevent unnecessary shocks, and would allow patients to live their lives normally with a defibrillator, confident that they would be warned before receiving a shock.

10 Claims, 7 Drawing Sheets

FIG. 5A
User Interface Inputs

FIG. 5B

User Interface Outputs

FIG. 6

DEFIBRILLATOR WITH WARNING INDICATORS

BACKGROUND OF THE INVENTION

Millions of Americans are dependent on an implanted defibrillator to save their lives in the case of a cardiac arrest. However, defibrillators do not warn the patient before delivering a shock to the heart. Doctors compare the feeling of a delivered shock to getting kicked in the chest by a mule. (https://abcnews.go.com/Health/HeartRythmTreatment/story?id=5213935) If a shock is delivered when a patient is in a vulnerable situation, serious injury or death could occur.

Take, for instance, a patient who is exercising at a gym. Suppose the patient lifts weights for about 45 minutes, thereby causing his heart rate to rise. Suppose the patient then runs on the treadmill, causing his body to labor significantly and his heart rate to continue to rise. In a state of fatigue, the patient may not be alert enough to prepare himself for a shock. If the defibrillator detects an irregular rhythm exceeding a heart rate threshold, it shocks the patient without warning. The force, paired with his complete unawareness that the shock would be delivered, may cause the patient to fall off the treadmill while it is still in operation, resulting in serious injury. Emergency Medical Services would need to be called, and they would perhaps even need to bring the patient to the hospital. The defibrillator is supposed to prevent cardiac emergencies, and thereby avoid the need for Emergency Medical Services. In this instance, because of the lack of warning prior to shock administration of existing defibrillators, the EMS was forced to come regardless.

In another scenario, a patient goes on a bike ride. If the exercise causes his heart rate to exceed a threshold, the defibrillator will deliver a shock again, without warning. Rather than just falling to the ground like the patient on the treadmill, the cycling patient could get his legs caught in the bike as he fell, resulting in bruises or perhaps broken bones. In this scenario even greater harm could be suffered by the patient, depending on his position. If the patient was riding in the bike lane parallel to the road, leaning left on his fall would cause the patient to swerve into traffic. Obviously, being hit by a car in that scenario would cause grave injuries and perhaps even death. Once again, the defibrillator caused harm to the patient, simply because it did not warn the patient prior to administering the shock.

A patient driving a car would present perhaps an even more dangerous problem. The World Health Organization estimates that 1.35 million people die from car accidents. They also recognize that a leading risk factor for car accidents is distracted driving. (https://www.who.int/newsroom/fact-sheets/detail/road-traffic-injuries)) If a patient were operating a vehicle when the shock is administered, the patient would undoubtedly become distracted. Without receiving a warning from the defibrillator, the patient would have no reason to pull to the side of the road and brace himself for a shock. Instead, the patient would not only hurt himself but other drivers as well.

The National Endowment for the Arts estimates that 6.9% of the professional workforce work as artists. (https://www.arts.gov/news/2011/nea-announces-new-research-note-artists-workforce) As a sizable portion of the workforce, artists either prepare works beforehand and sell them, or they perform to live audiences. In both instances, the sudden jolt from a defibrillator would prove frustrating, not to mention embarrassing. If an artist is painting, one wrong brushstroke could ruin the painting. A shock could cause the patient to throw away a masterpiece that he had spent days if not weeks working on. In the field of performance art, an unexpected shock would be significantly worse. Dancers work in unison on stage to choreograph a beautiful work of art. If a shock were to be delivered to one of the dancers the jolt would ruin the symmetry of the dance, embarrassing the dancers in front of an audience that could total thousands of people. In addition, such a noticeable mistake by a danser could result in lost friendships with other dancers, and perhaps even a job. Similarly, a musician at a concert must maintain strong focus in order to play without errors. The unexpected shock would disrupt such focus, resulting in similar undesirable consequences.

Operating power tools by a patient with a defibrillator can also be very dangerous. Power tools cause 400,000 emergency room visits every year in the United States. (https://www.frankeidson.com/practice-areas/workers-compensation/workplace-accidents/power-tool-accidents/) The focus and precision required to use such tools proves challenging even for those who do not require a defibrillator. Naturally, patients using power tools put themselves at an even greater risk because they could lose control of the tools when they receive a shock unexpectedly. For example, a person operating a chainsaw could cut off a limb after being startled by an unexpected shock.

Perhaps the most dangerous scenario involves patients who work at high elevations. Roofers are tasked with replacing the shingles on buildings, often forced to bend down and hammer them in in an awkward position. An unexpected shock could cause them to fall off the roof, plummeting to the ground from heights of at least 15-20 feet. Workers on skyscrapers would experience a similar reaction, except, that, they would most certainly die if they were to fall from the scaffolding after receiving an unexpected shock.

Moreover, existing defibrillators do not give patients the opportunity to adjust their behavior to avoid receiving a shock. A patient whose heart rate is approaching a threshold, therefore, does not have the opportunity to stop exercising and rest to prevent the threshold from being reached and to avoid receiving a shock. As a result, existing defibrillators often administer shocks that could have been avoided.

Accordingly, there exists a need for a defibrillator that has the ability to warn a patient immediately before delivering a shock so that the patient can prepare prior to receiving the shock, or to warn the patient whose heart rate is approaching the threshold so that the patient can alter behavior to avoid receiving the shock.

SUMMARY OF THE INVENTION

The present intention satisfies this need. The pacemaker/defibrillator of the present invention detects an irregular heart rhythm in its early stages so that the patient may alter his or her behavior to avoid a shock. The pacemaker/defibrillator will also be able to warn a user prior to shock administration if a shock is in fact needed.

Current pacemaker/defibrillators have the ability to measure the patient's heart rhythm. With the addition of a speaker, these pacemaker/defibrillators will now use the feature in order to warn a patient when they are near a required threshold to deliver a shock. This would prevent unnecessary shock administration if the patient listened to the device and attempted to calm down and allow his heart to return to a normal rhythm.

In the case of unavoidable shock, or if the patient is unable to allow his heart to return to a normal rhythm, the speaker would be used to at least notify the patient before the shock is delivered so that they can be prepared in a safe position to receive it.

DETAILED DESCRIPTION OF THE PREFERRED EMBODIMENTS

Figure 1:
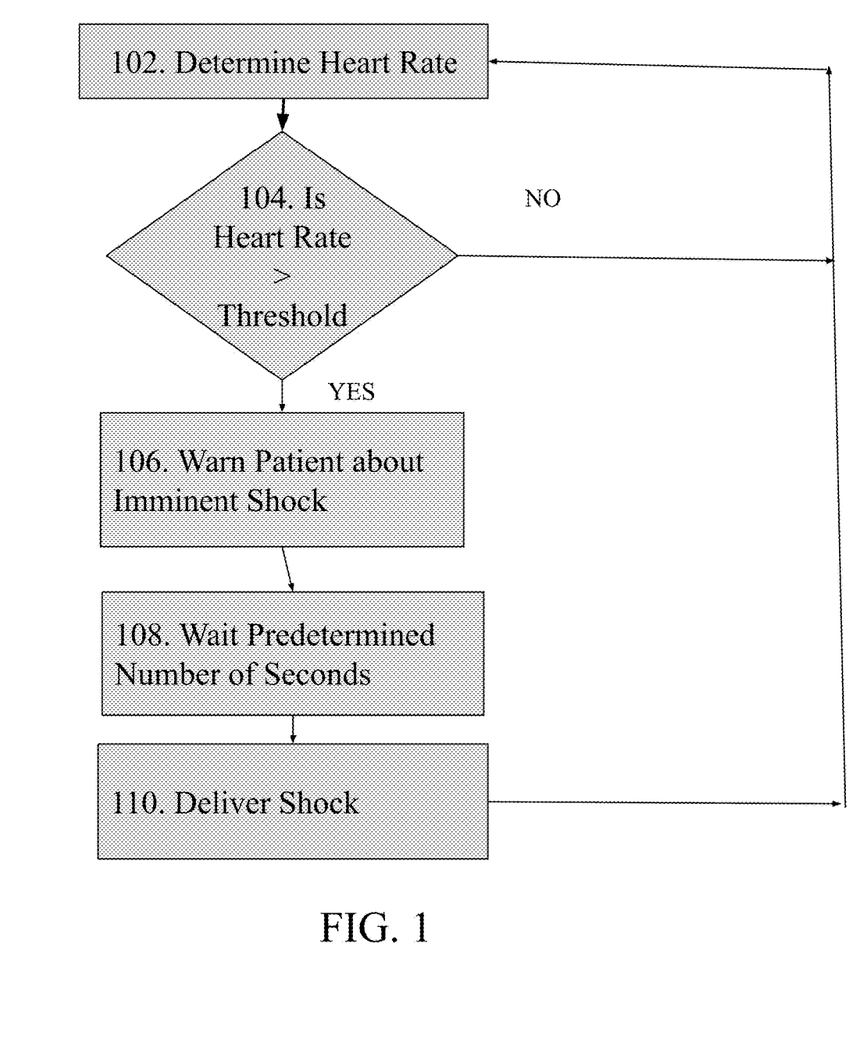
FIG. 1 is a flow diagram of an embodiment of a method of the present invention 100.

FIG. 1 is a flow diagram of an embodiment of a method of the present invention 100. In step 102, the patient's heart rate is detected by the defibrillator device. In step 104, the detected heart rate is compared to a threshold. In one embodiment, the threshold may be input to the memory of the defibrillator device by a medical professional or the patient through a user interface. If the patient's heart rate is less than the threshold, control returns to step 102. If the patient's heart rate is greater than the threshold, control proceeds to step 106. In step 106, a patient is warned of an imminent shock. In step 108, the defibrillator waits a predetermined number of seconds. In one embodiment, the predetermined number of seconds may be input to the memory of the defibrillator device by a medical professional. In step 110, the shock is delivered. Control then returns to step 102.

Figure 2:
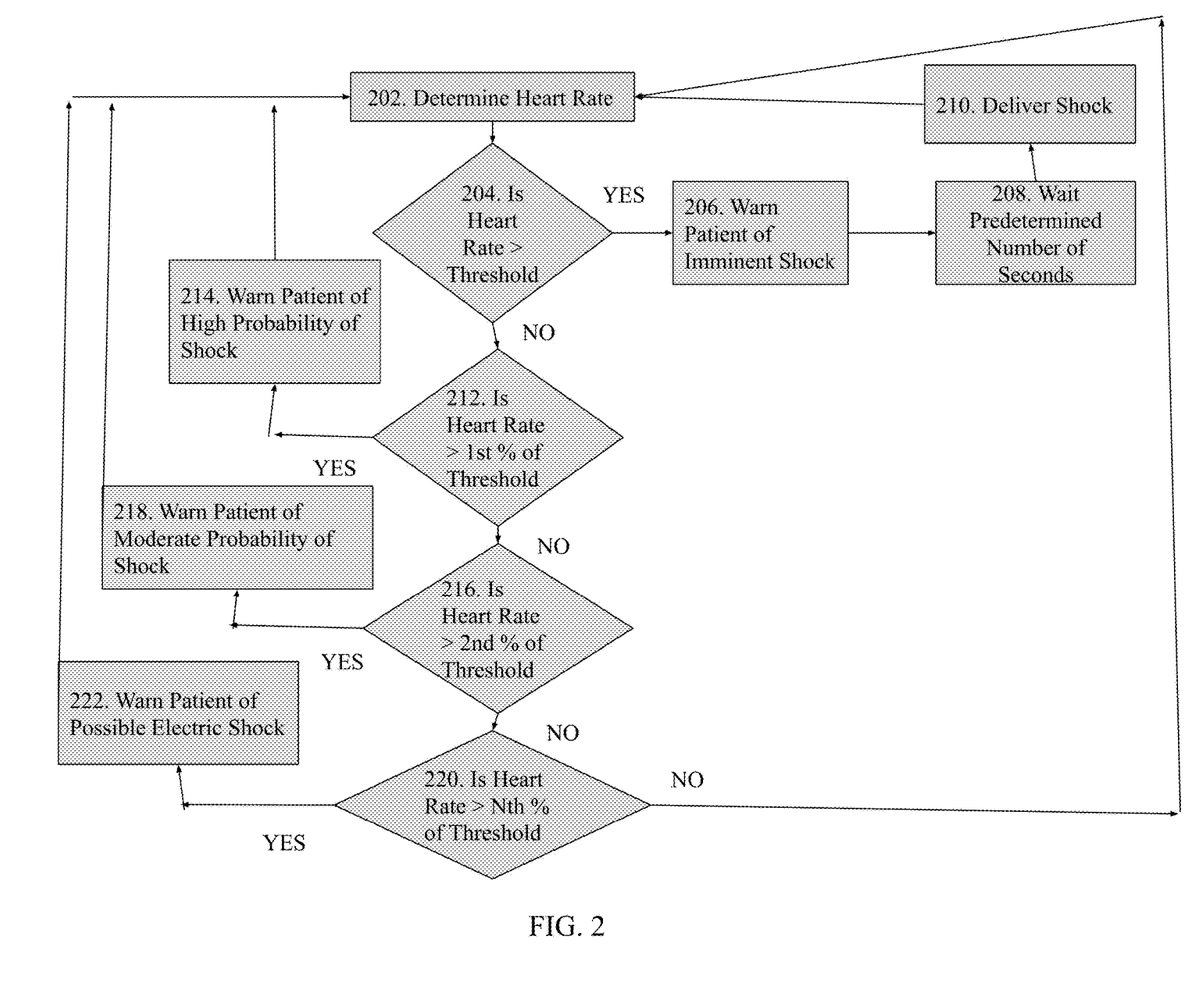
FIG. 2 is a flow diagram of another embodiment of a method of the present invention 200.

FIG. 2 is a flow diagram of another embodiment of a method of the present invention 200. In step 202, the patient's heart rate is determined. In step 204, the patient's heart rate is compared to a predetermined heart rate threshold. The heart rate threshold may be determined by a medical professional. If the heart rate is greater than heart rate threshold, control proceeds to step 206. If not, however, control proceeds to step 212. In step 206, the patient is warned of an imminent shock by a speaker, smartphone, smartwatch, or earbuds. In step 208, the processor waits a predetermined number of seconds. The predetermined wait time may be determined by a medical professional. In step 210, a shock is delivered. Control returns to step 202. In step 212, the heart rate determined in step 202 is compared to a first percentage of the predetermined heart rate threshold. This percentage may also be determined by a medical professional. If the heart rate is greater than the percentage of the threshold, control proceeds to step 214. If not, control proceeds to step 216. In step 214, the patient is warned of a high probability of shock in the near future by a speaker, smartphone, smartwatch, or earbuds. Control returns to step 202. In step 216, the heart rate is compared to a second and smaller percentage of the predetermined heart rate threshold. This percentage would also be determined by a medical professional. If the heart rate is greater than this second percentage of the predetermined heart rate threshold, control proceeds to step 218. If not, control proceeds to step 220. In step 218, the patient is warned of a moderate probability of shock in the near future by a speaker, smartphone, smartwatch, or earbuds. This enables a patient to adjust her behavior to avoid a shock e.g. resting. Control proceeds to step 202. The method executes in this manner until the heart rate is compared to an nth percentage of the threshold in step 220, where n is a positive integer. If the heart rate is greater than the nth percentage of the threshold, control proceeds to step 222. If not, control returns to step 202. The nth percentage of the threshold may be determined by a medical professional. In one embodiment, each of the n percentages is expected, to be smaller than the previous percentage. That is, the nth percentage may be less than the (n−1)th percentage. The severity of the warning will change based on the threshold that was exceeded. A warning issued by exceeding a higher threshold will be more severe than a warning issued by exceeding a lower threshold.

Figure 3:
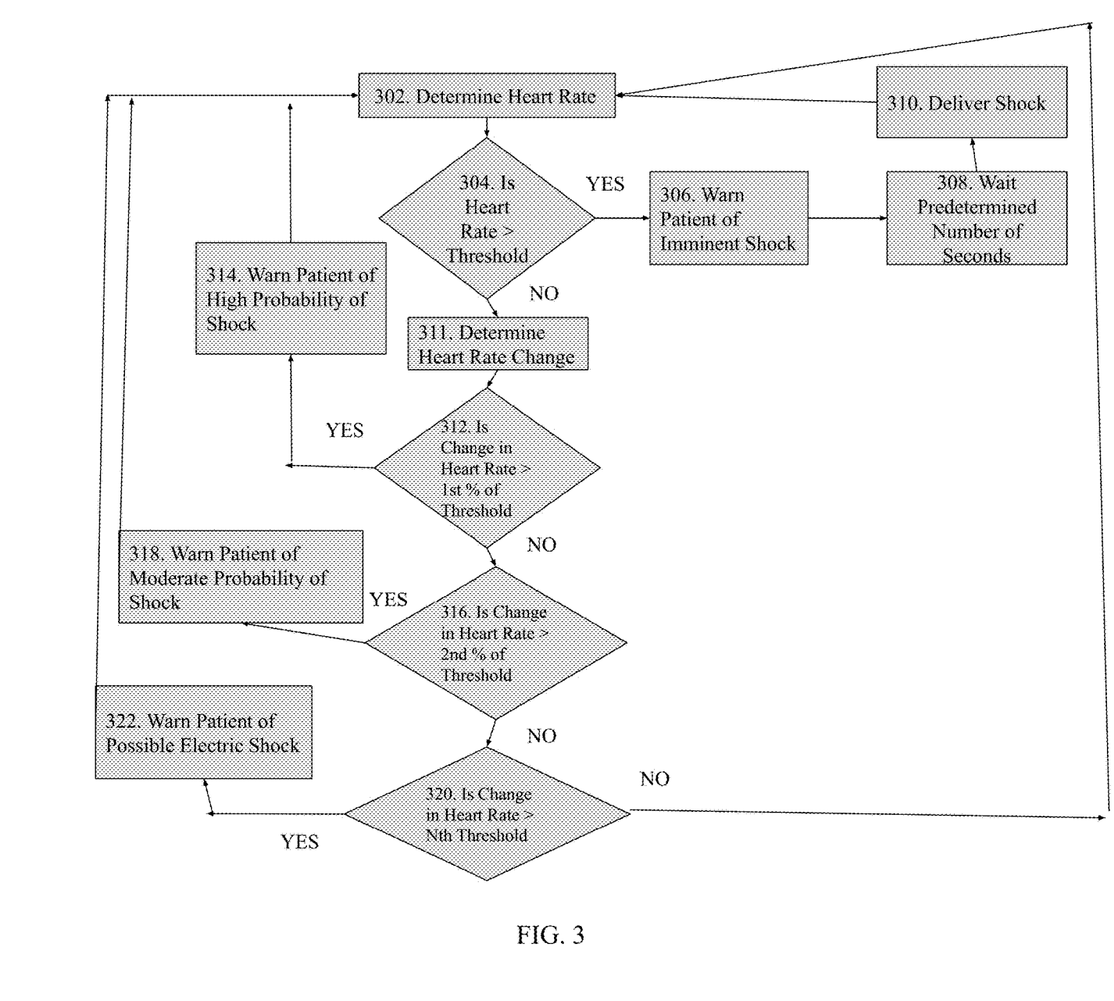
FIG. 3 is a flow diagram of another embodiment of a method of the present invention 300.

FIG. 3 is a flow diagram of another embodiment of a method of the present invention 300. In step 302, the patient's heart rate is determined. In step 304, the heart rate is compared to a predetermined threshold. This threshold may be determined by a medical professional. If the heart rate is greater than the threshold, control proceeds to step 306. If not, control proceeds to step 311. In step 306, the patient is warned of imminent shock by a speaker, smartphone, smartwatch, or earbuds. In step 308, the processor waits a predetermined number of seconds. This wait time may be determined by a medical professional. In step 310, the defibrillator delivers a shock. In step 311, the patient's heart rate is determined again and the change in heart rate from the heart rate observed in step 302 to the heart rate observed in step 311 is determined. In step 312 the change in heart rate is compared to a first threshold change in heart rate. This threshold change may be determined by a medical professional. If the change in monitored heart rate is greater than this first threshold, control proceeds to step 314. If not, control proceeds to step 316. In step 314, the patient is warned of a high shock probability in the near future by a speaker, smartphone, smartwatch, or earbuds. Control proceeds to step 302. In step 316, the change in heart rate is compared to a second and smaller change in heart rate threshold. If the change in monitored heart rate is greater than this second heart rate threshold, control proceeds to step 318. If not, control proceeds to step 320. In step 318, the patient is warned of a moderate probability of shock in the near future by a speaker, smartphone, smartwatch, or earbuds. The method executes in this manner until the heart rate change is compared to an nth threshold in step 320, where n is a positive integer. In one embodiment, each of the n percentages is smaller than the preceding percentage. If the heart rate change exceeds the nth threshold, control proceeds to step 322 where the patient is warned. Otherwise, control proceeds to step 302.

Figure 4:
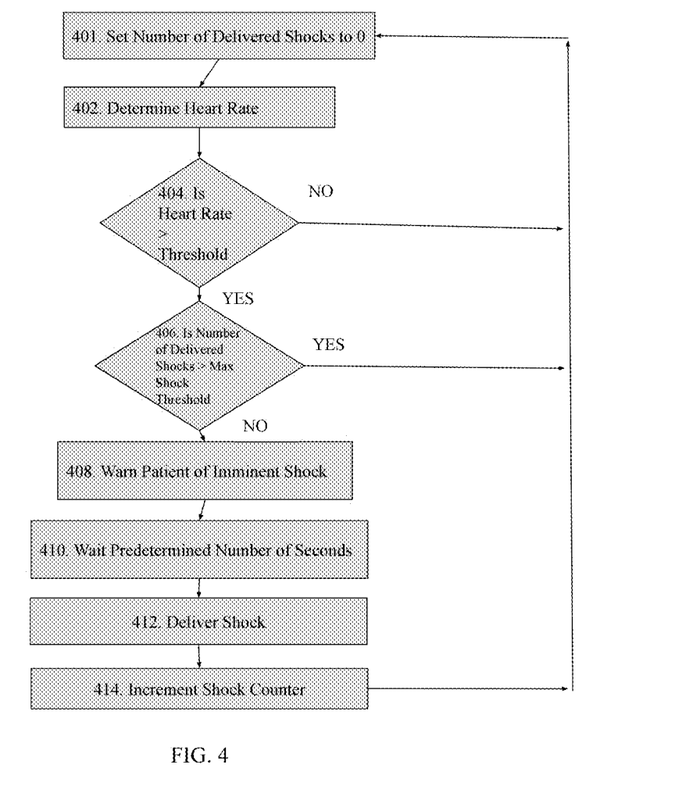
FIG. 4 is a flow diagram of another embodiment of a method of the present invention 400.

FIG. 4 is a flow diagram of another embodiment of a method of the present invention 400. In step 401 the number of delivered shocks is set to zero in the memory. In step 402, the heart rate is determined. In step 404, the heart rate is compared to a predetermined threshold. If the heart rate is less than the predetermined threshold, control returns to step 402. If the heart rate is greater, however, control proceeds to step 406. In step 406, the number of shocks that have been delivered in a certain time period is compared to a predetermined maximum number of shocks that can be delivered over that time period. This predetermined maximum may be input by a medical professional. If this threshold is less than the number of shocks delivered, control returns to step 402. If the number of delivered shocks in the time period is less than the threshold, control proceeds to step 408. Otherwise, control proceeds to step 402. In step 408, the patient is warned of imminent shock by a speaker 612, earbuds 614, smartphone 616, or smartwatch 618. In step 410, the processor waits a predetermined number of seconds. In step 412, the shock is delivered. In step 414, the shock counter is incremented by one. Control then proceeds to step 402.

Figure 5A:
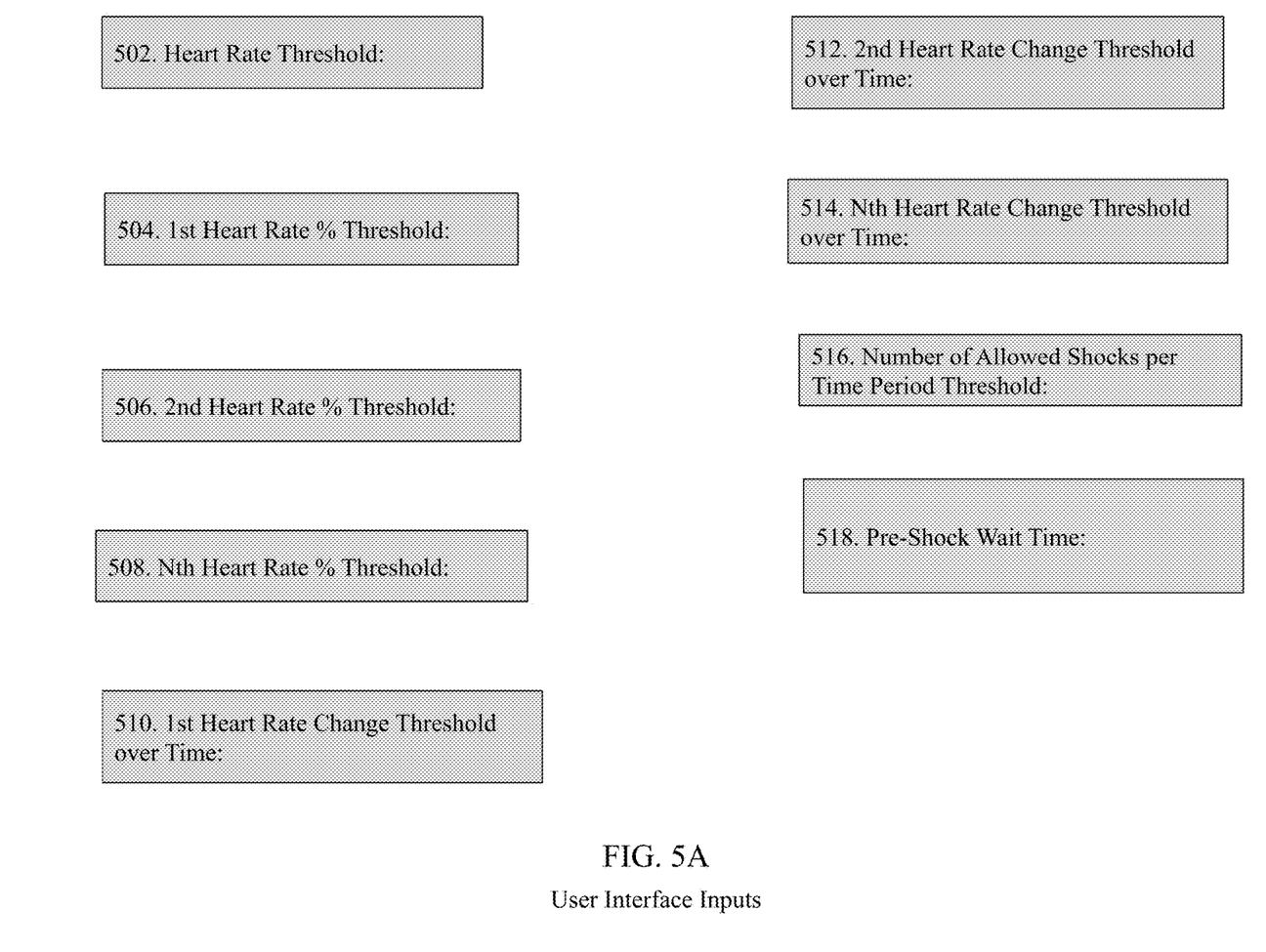
FIG. 5A is a diagram of an embodiment of a user interface 500 of the present invention showing the user interface inputs.

FIG. 5A is a diagram of a user interface 500 of the present invention. It can be implemented on a smartphone application or a website in order to personalize a patient's defibrillator experience. Field 502 is a heart rate threshold that may be input by a user(e.g. medical professional, patient). Field 504 is a first percentage of a heart rate threshold 502. Field 506 is a second percentage of a heart rate threshold 502. Field 508 is an nth percentage of a heart rate threshold 502. Field 510 is a first heart rate change threshold. Field 512 is a second heart rate change threshold. Field 514 is an nth heart rate change threshold Field 516 is a threshold of the number of shocks over a time period that may be delivered to the patient. Field 518 is a wait time from the time the patient is warned until the time the shock is delivered.

Figure 5B:
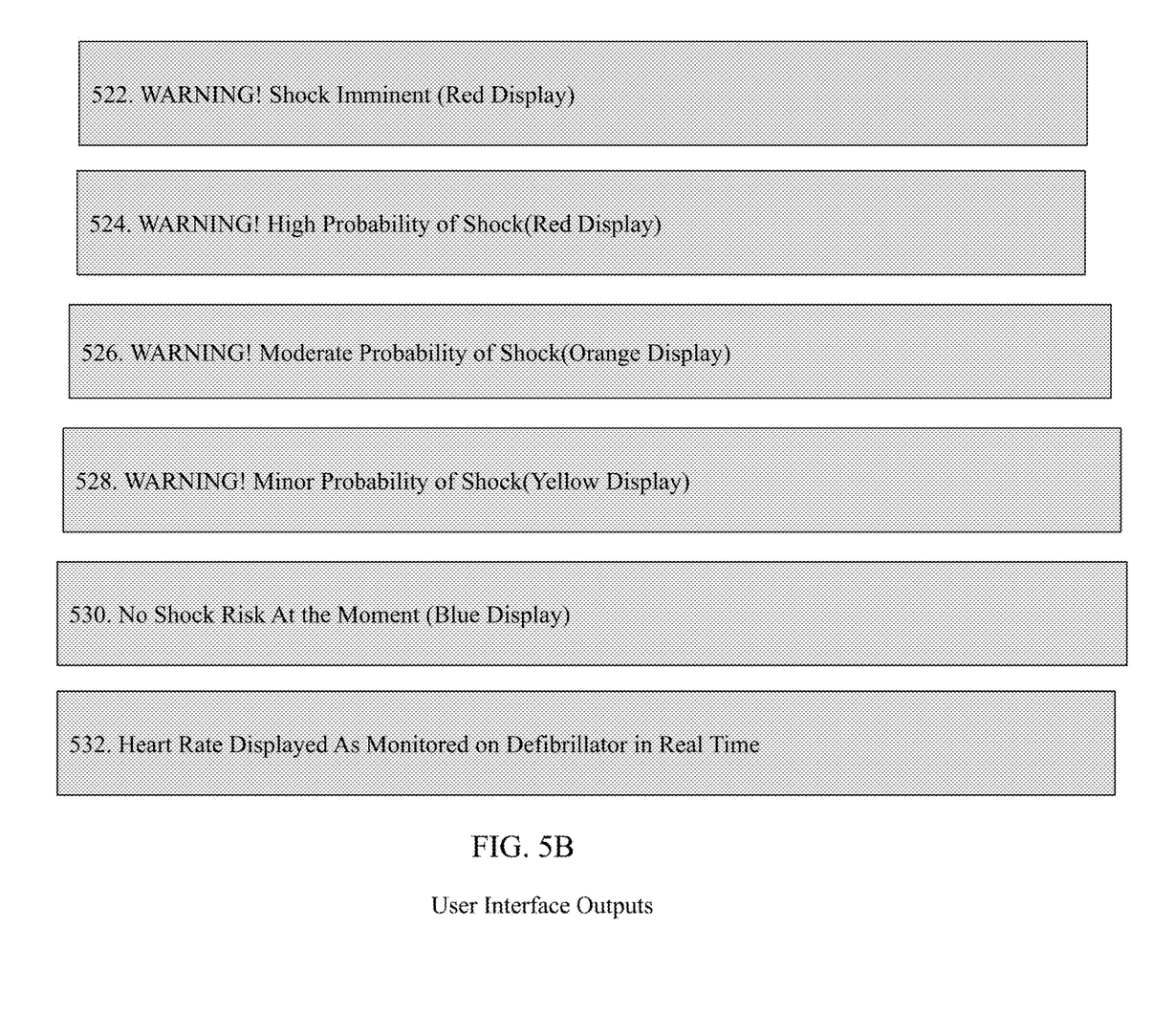
FIG. 5B is a diagram of an embodiment of a user interface of the present invention showing the user interface outputs.is a diagram of an embodiment of a user interface 500 of the present invention.

FIG. 5B is a diagram of a user interface 550 of the present invention. Both the warning and informative messages found in user interface 550 can be vocalized/displayed on speakers, earbuds, smartphones, and smartwatches alike. Message 522 warns the patient of an imminent shock. In the case of a smartphone or smartwatch, the display may also turn a bright red. Message 524 warns a patient of a high probability of shock in the near future. In the case of a smartphone or smartwatch, the display may turn red. Message 526 warns a patient of a moderate probability of shock. In the case of a smartphone or smartwatch, the display may turn orange. Message 528 warns a patient of a minor probability of shock. In the case of a smartphone or a smart watch, the display may turn yellow. Message 530 is the most common message expected to be displayed. It confirms for the patient that they are at very low risk of shock at the moment, indicated by a green display in the case of a smartphone or smartwatch. Message 532 is the patient's heart rate as it is monitored in real time by the defibrillator. This display would only be applicable to a smartwatch, smartphone, or other devices that have a display screen.

Figure 6:
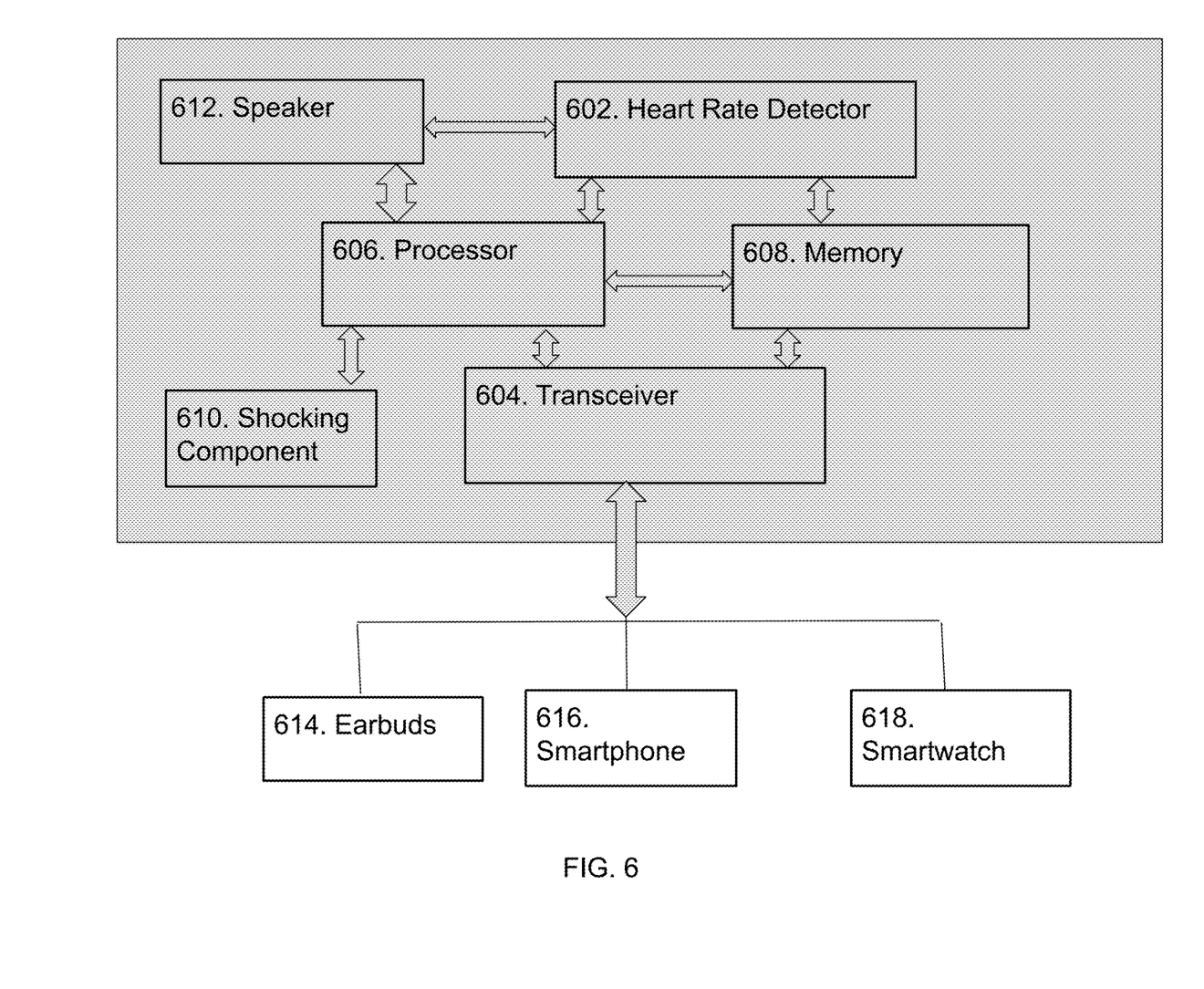
FIG. 6 is a diagram of an embodiment of a defibrillator 600 of the present invention.

FIG. 6 is a diagram of the defibrillator 600 of the present, invention. The defibrillator comprises a heart rate detector 602 that determines the heart rate in steps 102, 202, 208, 214, and 302 from the previous figures. The defibrillator further comprises a transceiver 604. The transceiver 604 is electrically connected to external peripheral devices such as earbuds 614, smartphone 616, and/or a smartwatch 618. Warnings of elevated heart rate, imminent shock, etc. in steps 106, 206, 212, 218, and 310 are transmitted via the transceiver 614 to these external devices. Defibrillator 600 also comprises a processor 606 that executes instructions for the methods described in FIGS. 1-4. The defibrillator also comprises a memory 608 which stores data such as the heart rate thresholds, heart rate change thresholds, delay times (before delivering a shock), and other parameters that control the operation of the defibrillator 600. These parameters could be input by a medical professional or the patient. Memory 608 also stores measured and calculated values such as heart rate, heart rate change, etc. Part 610 represents the component that delivers a shock. The defibrillator 600 may also comprise an internal speaker 612, which emits different sounds for different warnings. In one embodiment, a speaker emits one tone or volume when a shock is about to be delivered and another tone or volume when a heart rate is approaching the shock threshold. Processor 606 is electrically connected to a speaker 612, heart rate detector 602, memory 608, transceiver 604, and shock component 610. Heart rate detector 602 is electrically connected to the processor 606 and the memory 608. Transceiver 604 is electrically connected to the processor 606 and the memory 608 as well. The transceiver is also connected to external devices such as earbuds 614, smartphone 616, and smartwatch 618.

The invention claimed is:

1. An implantable defibrillator comprising:
   a. at least one component for initiating a shock to a patient;
   b. at least one wire connecting at least one shock component to the patient's heart;
   c. at least one detector for detecting a heart rate of a patient;
   d. at least one processor electrically connected to at least one shocking component and at least one heart rate detector;
   e. at least one non-transient memory electrically connected to said heart rate detector and said processor, said at least one memory stores a first heart rate threshold and a program that when executed, performs the following steps:
      i. determining a heart rate of the patient;
      ii. if said determined heart rate is greater than said first heart rate threshold,
         iii. sending a first warning indication to the patient;
         iv. waiting a predetermined amount of time; and
         v. initiating a shock to the patient;
      vi. if said determined heart rate is not greater than said first heart rate threshold,
         vii determining a rate of change of the heart rate of the patient;
         viii if said determined heart rate change is greater than a first heart rate change threshold, sending a second warning indicator to the patient;
         ix. if said determined heart rate change is greater than a second heart rate change threshold, sending a third warning indicator to the patient.

2. An implantable defibrillator as in claim 1 further comprising a speaker wherein the speaker performs the step of sending a warning indication to the patient by emitting a first warning sound for the speaker.

3. An implantable defibrillator as in claim 1 further comprising at least one transceiver and one or more external devices wherein said step of sending a first warning indicator to the patient comprises sending a first warning signal to at least one of said external devices.

4. An implantable defibrillator as in claim 3 wherein said one or more external device consists of one or more of the following: an earbud, a smartphone; and a smartwatch.

5. An implantable defibrillators as in claim 1 wherein said program, when executed, also performs the additional following steps:
   a. if said determined heart rate is greater than a second heart rate threshold, wherein said second heart rate threshold is a fraction of said first heart rate threshold,
   b. sending a second warning indicator to the patient.

6. An implantable defibrillator as in claim 5 wherein said program, when executed also performs the following steps:
   a. if said determined heart rate is greater than a third heart rate threshold, wherein said third heart rate threshold is a fraction of said second heart rate threshold,
   b. sending a third warning indicator to the patient.

7. An implantable defibrillator as in claim 6 wherein said first warning indicator indicates that a shock is imminent, said second warning indicator indicates there is a high probability of a shock and said third warning indicator indicates that there is a moderate probability of a shock and wherein said first warning indicator has a tone and volume that differs from a tone and volume of said second and third warning indicators.

8. An implantable defibrillator as in claim 1 wherein said first warning indicator indicates
that a shock is imminent, said second warning indicator indicates there is a high
probability of a shock and said third warning indicator indicates that there is a moderate
probability of a shock and wherein said first warning indicator has a tone and volume
that differs from a tone and volume of said second and third warning indicators.

9. An implantable defibrillator as in claim 1 wherein said at least one memory includes a variable for counting the number of delivered shocks to the patient wherein said program, when executed, performs the additional steps of incrementing said shock counter variable each time a shock is delivered to the patient; repeating steps 1 through 5 of claim 1 until said shock counter variable exceeds a shock threshold.

10. An implantable defibrillator as in claim 3 wherein at least one of said external devices comprises:
   a. at least one processor and at least one non-transient memory electrically connected to said processor, said memory comprises code that when executed performs the steps of
      i. displaying an interface to the patient wherein the interface display includes one or more of the following:
         1. One or more first fields for specifying corresponding one or more heart rate thresholds;
         2. One or more second fields for specifying corresponding one or more heart rate change thresholds;
         3. At least one third field for specifying the number of shocks that are permitted within a time period;
         4. At least one fourth field specifying the amount of time to wait after delivering said first warning indicator before initiating a shock to the patient;
         5. One or more fields corresponding to one or more shock warning indicators; and
         6. At least one field showing the heart rate of the patient.

* * * * *